United States Patent
Soliman et al.

(10) Patent No.: US 11,540,986 B2
(45) Date of Patent: Jan. 3, 2023

(54) PERSONAL CARE COMPOSITION

(71) Applicant: Colgate-Palmolive Company, New York, NY (US)

(72) Inventors: Nadia Soliman, East Brunswick, NJ (US); Kathryn Pope, Califon, NJ (US); Sandra Wadeer, Flanders, NJ (US); Joan Gambogi, Hillsborough, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 16/768,976

(22) PCT Filed: Dec. 7, 2017

(86) PCT No.: PCT/US2017/065091
§ 371 (c)(1),
(2) Date: Jun. 2, 2020

(87) PCT Pub. No.: WO2019/112587
PCT Pub. Date: Jun. 13, 2019

(65) Prior Publication Data
US 2020/0368123 A1    Nov. 26, 2020

(51) Int. Cl.
| | | |
|---|---|---|
| *A61K 8/26* | (2006.01) | |
| *A61K 8/28* | (2006.01) | |
| *A61K 8/34* | (2006.01) | |
| *A61K 8/37* | (2006.01) | |
| *A61K 8/73* | (2006.01) | |
| *A61K 8/891* | (2006.01) | |
| *A61Q 15/00* | (2006.01) | |

(52) U.S. Cl.
CPC .................. *A61K 8/26* (2013.01); *A61K 8/28* (2013.01); *A61K 8/342* (2013.01); *A61K 8/375* (2013.01); *A61K 8/732* (2013.01); *A61K 8/891* (2013.01); *A61Q 15/00* (2013.01); *A61K 2800/26* (2013.01)

(58) Field of Classification Search
CPC . A61K 8/26; A61K 8/28; A61K 8/891; A61K 2800/596; A61Q 15/00
See application file for complete search history.

(56) References Cited

U.S. PATENT DOCUMENTS

| | | |
|---|---|---|
| 5,547,661 A | 8/1996 | Sun et al. |
| 5,972,319 A | 10/1999 | Linn et al. |
| 6,007,799 A | 12/1999 | Lee et al. |
| 6,350,460 B1 | 2/2002 | Andrews et al. |
| 6,403,067 B1 | 6/2002 | Schamper et al. |
| 6,403,069 B1 | 6/2002 | Chopra et al. |
| 6,488,919 B1 | 12/2002 | Murphy et al. |
| 6,759,032 B2 | 7/2004 | Murphy et al. |
| 2006/0029624 A1 | 2/2006 | Banowski et al. |
| 2009/0220444 A1 | 9/2009 | Teckenbrock et al. |
| 2013/0280175 A1* | 10/2013 | Banowski .............. A61Q 15/00 424/68 |
| 2014/0086848 A1 | 3/2014 | Tamarkin et al. |
| 2015/0182424 A1* | 7/2015 | Schmit .................. A61Q 15/00 424/47 |
| 2016/0296453 A1 | 10/2016 | Anconi et al. |
| 2019/0183780 A1 | 6/2019 | Cheng et al. |

FOREIGN PATENT DOCUMENTS

| | | | |
|---|---|---|---|
| EP | 2949313 | 12/2015 | |
| GB | 2080678 | 2/1982 | |
| WO | 1998/043605 | 10/1998 | |
| WO | 2000/053151 | 9/2000 | |
| WO | 2004/112739 | 12/2004 | |
| WO | WO-2004112739 A1 * | 12/2004 | .............. A61K 8/39 |
| WO | 2008/036587 | 7/2008 | |
| WO | 2017/196299 | 11/2017 | |
| WO | WO-2017196299 A1 * | 11/2017 | .............. A61K 8/26 |

OTHER PUBLICATIONS

International Search Report and the Written Opinion of the International Searching Authority issued in International Application PCT/US2017/065091 dated May 15, 2018.

* cited by examiner

*Primary Examiner* — Andrew S Rosenthal

(57) ABSTRACT

An opaque antiperspirant composition, including an antiperspirant active, a high HLB surfactant, an emollient, and a gelling agent, wherein the high HLB surfactant includes a high HLB glyceryl monostearate mixture.

12 Claims, No Drawings

PERSONAL CARE COMPOSITION

BACKGROUND

Personal care compositions, such as antiperspirant or deodorant compositions and dual purpose antiperspirant-deodorant compositions, may be used to reduce body odor. Antiperspirant or deodorant compositions may be applied to axillary (underarm) regions to prevent or treat perspiration, limit the growth of odor-causing bacteria, or apply a fragrance. Antiperspirant or deodorant compositions may be delivered topically as roll-on, gel, cream, stick or aerosol formulations. However, depending on their ingredients, the antiperspirant or deodorant compositions may also leave an unsightly white residue on the skin or clothing after being applied.

Accordingly, there is a desire for stable and effective antiperspirant or deodorant compositions that are also formulated to reduce or eliminate the amount of white residue left after application.

BRIEF SUMMARY

This section is intended merely to introduce a simplified summary of some aspects of one or more embodiments of the present disclosure. Further areas of applicability of the present invention will become apparent from the detailed description provided hereinafter. This summary is not an extensive overview, nor is it intended to identify key or critical elements of the present teachings, nor to delineate the scope of the disclosure. Rather, its purpose is merely to present one or more concepts in simplified form as a prelude to the detailed description below.

The foregoing and/or other aspects and utilities embodied in the present disclosure may be achieved by an opaque antiperspirant composition including an antiperspirant active; a high HLB surfactant; an emollient; and a gelling agent, wherein the high HLB surfactant comprises a high HLB glyceryl monostearate mixture.

In another embodiment, the opaque antiperspirant composition is opaque before application but is configured to appear transparent after being applied to the skin and/or reduce an amount of white residue left after application.

In another embodiment, the high HLB surfactant includes Steareth-21, and a ratio of the high HLB glyceryl monostearate mixture to the Steareth-21 is from 4:1 to 10:1.

In another embodiment, the opaque antiperspirant composition further includes a carrier and an inert filler.

In another embodiment, the inert filler includes at least one of tapioca starch and silica.

In another embodiment, the opaque antiperspirant composition includes from 5 weight % to 30 weight % of the antiperspirant active, based on a total weight of the opaque antiperspirant composition.

In another embodiment, the opaque antiperspirant composition includes from 1 weight % to 15 weight % of the high HLB surfactant, based on the total weight of the opaque antiperspirant composition.

In another embodiment, the opaque antiperspirant composition includes from 2 weight % to 20 weight % of the emollient, based on the total weight of the opaque antiperspirant composition.

In another embodiment, the antiperspirant active includes at least one of aluminum chlorohydrate, aluminum chloride, aluminum chlorohydroxide, and aluminum zirconium.

In another embodiment, the antiperspirant active includes aluminum zirconium tetrachlorohydrex glycine.

In another embodiment, the emollient includes at least one of cetyl alcohol, isopropyl myristate, and dodecamethylpentasiloxane.

In another embodiment, the high HLB surfactant consists essentially of a mixture of Steareth-21 and a high HLB glyceryl monostearate mixture.

In another embodiment, the high HLB glyceryl monostearate mixture includes polyglyceryl-6 palmitate/succinate.

The foregoing and/or other aspects and utilities embodied in the present disclosure may also be achieved by an antiperspirant composition, including from 5 weight % to 30 weight % of an antiperspirant active, based on a total weight of the antiperspirant composition; from 1 weight % to 15 weight % of a high HLB surfactant, based on the total weight of the antiperspirant composition; from 2 weight % to 20 weight % of an emollient, based on the total weight of the antiperspirant composition; and an inert filler, wherein the antiperspirant composition is opaque, wherein the high HLB surfactant comprises at least one of Steareth-21 and a high HLB glyceryl monostearate mixture, and wherein the high HLB glyceryl monostearate mixture comprises polyglyceryl-6 palmitate/succinate.

In another embodiment, the high HLB surfactant consists essentially of a mixture of Steareth-21 and a high HLB glyceryl monostearate mixture.

In another embodiment, the antiperspirant active includes aluminum zirconium tetrachlorohydrex glycine.

DETAILED DESCRIPTION

Reference will now be made in detail to the various embodiments in the present disclosure. The embodiments are described below to provide a more complete understanding of the components, processes, compositions, and apparatuses disclosed herein. Any examples given are intended to be illustrative, and not restrictive. However, it will be apparent to one of ordinary skill in the art that the invention may be practiced without these specific details. In other instances, well-known methods, procedures, and components have not been described in detail so as not to unnecessarily obscure aspects of the embodiments.

Throughout the specification and claims, the following terms take the meanings explicitly associated herein, unless the context clearly dictates otherwise. Phrases such as "in some embodiments" and "in an embodiment" as used herein do not necessarily refer to the same embodiment(s), though they may. Furthermore, the phrases "in another embodiment" and "in certain embodiments" as used herein do not necessarily refer to a different embodiment, although they may. As described below, various embodiments may be readily combined, without departing from the scope or spirit of the present disclosure.

As used herein, the term "or" is an inclusive operator, and is equivalent to the term "and/or," unless the context clearly dictates otherwise. The term "based on" is not exclusive and allows for being based on additional factors not described, unless the context clearly dictates otherwise. In the specification, the recitation of "at least one of A, B, and C," includes embodiments containing A, B, or C, multiple examples of A, B, or C, or combinations of A/B, A/C, B/C, A/B/B/B/B/C, AB/C, etc. In addition, throughout the specification, the meaning of "a," "an," and "the" include plural references. The meaning of "in" includes "in" and "on."

It will also be understood that, although the terms first, second, etc. may be used herein to describe various elements, these elements should not be limited by these terms. These terms are only used to distinguish one element from another. For example, a first object, component, or step could be termed a second object, component, or step, and, similarly, a second object, component, or step could be termed a first object, component, or step, without departing from the scope of the invention. The first object, component, or step, and the second object, component, or step, are both, objects, component, or steps, respectively, but they are not to be considered the same object, component, or step. It will be further understood that the terms "includes," "including," "comprises" and/or "comprising," when used in this specification, specify the presence of stated features, steps, operations, elements, and/or components, but do not preclude the presence or addition of one or more other features, steps, operations, elements, components, and/or groups thereof. Further, as used herein, the term "if" may be construed to mean "when" or "upon" or "in response to determining" or "in response to detecting," depending on the context.

All physical properties that are defined hereinafter are measured at 20° to 25° Celsius unless otherwise specified.

When referring to any numerical range of values herein, such ranges are understood to include each and every number and/or fraction between the stated range minimum and maximum, as well as the endpoints. For example, a range of 0.5-6.0% would expressly include all intermediate values of, for example, 0.6%, 0.7%, and 0.9%, all the way up to and including 5.95%, 5.97%, and 5.99%, among many others. The same applies to each other numerical property and/or elemental range set forth herein, unless the context clearly dictates otherwise.

Additionally, all numerical values are "about" or "approximately" the indicated value, and take into account experimental error and variations that would be expected by a person having ordinary skill in the art. It should be appreciated that all numerical values and ranges disclosed herein are approximate values and ranges, whether or not "about" is used in conjunction therewith.

Unless otherwise specified, all percentages and amounts expressed herein and elsewhere in the specification should be understood to refer to percentages by weight. The amounts given are based on the active weight of the material.

With regard to procedures, methods, techniques, and workflows that are in accordance with some embodiments, some operations in the procedures, methods, techniques, and workflows disclosed herein may be combined and/or the order of some operations may be changed.

Conventionally, many personal care compositions, such as deodorants or antiperspirants, may be formulated as translucent or clear gels that appear transparent or colorless when applied to the skin. However, in order to achieve a translucent or clear gel, the formulation may be limited to specific ingredients or exclude otherwise desirable emollients or additives. For example, to achieve a clear gel a formulation may exclude inert fillers that contribute to a dry feeling upon application of the personal care composition. Similarly, a clear gel may avoid specific emulsifiers or emollients that would otherwise contribute to the stability of the personal care composition during storage.

As described herein, the present disclosure provides a personal care composition embodied as an opaque cream that is nonetheless formulated or configured to appear transparent or colorless after being applied to the skin and/or reduce the amount of white residue left on skin or clothing after application. In addition, the personal care composition is configured to have high antiperspirant efficacy and to be stable during storage and repeated freeze/thaw cycles.

As used herein, the term "opaque" and "opaque cream" refers to a personal care composition that is not transparent or significantly translucent. That is, it may be substantially impenetrable to light or may allow no more than 25% of applied light to pass through a three millimeter thickness of the composition.

As used herein, the term "antiperspirant composition" is used to describe personal care compositions that function as antiperspirant compositions, deodorant compositions, or as dual purpose antiperspirant-deodorant compositions.

In certain embodiments, the personal care composition is an antiperspirant composition including a carrier, an emollient, a gelling agent, a surfactant, and an antiperspirant active.

The antiperspirant composition may be provided as an oil in water emulsion. In other embodiments, the antiperspirant composition may be anhydrous.

The antiperspirant composition may include one or more carriers or solvents. For example, the antiperspirant composition may be provided as an oil-in-water emulsion using primarily water as the carrier. In other embodiments, the carrier may include other co-solvents which are miscible with water. However, in various preferred embodiments, the carrier consists only of water or consists essentially of water, such as a carrier that consists of at least 99% water.

In one embodiment, the amount of carrier in the antiperspirant composition is the amount needed to make a 100% by weight composition after all of the ingredients, including any optional ingredients, are added to the composition. For example, the antiperspirant and/or deodorant composition may include at least 1 weight %, at least 5%, at least 10 weight %, at least 15 weight %, at least 20 weight %, at least 25 weight %, or at least 30 weight % of a carrier based on the total weight of the antiperspirant and/or deodorant composition. In other examples, the antiperspirant composition include from about 5 weight % to about 40 weight % water or from about 10 weight % to about 35 weight % water. In one preferred embodiment, the antiperspirant and/or deodorant composition include about 32 weight % water, based on the total weight of the antiperspirant and/or deodorant composition.

The antiperspirant composition includes one or more emollients. For example, the antiperspirant composition may include volatile and non-volatile emollients in any desired amount to achieve a desired emollient effect. Several emollients are known in the art and are used to impart a soothing effect on the skin. Examples of non-volatile emollients include non-silicone and silicone emollients. Examples of non-volatile, non-silicone emollients include C12-15 alkyl benzoate. A non-volatile silicone material can be a polyethersiloxane, polyalkyarylsiloxane or polyethersiloxane copolymer. An illustrative non-volatile silicone material is phenyl trimethicone. Non-limiting examples of emollients can be found in U.S. Pat. No. 6,007,799. Examples include, but are not limited to, PPG-14 butyl ether, PPG-15 stearyl ether, PPG-3 myristyl ether, stearyl alcohol, stearic acid, glyceryl monoricinoleate, isobutyl palmitate, glyceryl monostearate, isocetyl stearate, sulphated tallow, oleyl alcohol, propylene glycol, isopropyl laurate, mink oil, sorbitan stearate, cetyl alcohol, hydrogenated castor oil, stearyl stearate, hydrogenated soy glycerides, isopropyl isostearate, hexyl laurate, dimethyl brassylate, decyl oleate, diisopropyl adipate, n-dibutyl sebacate, diisopropyl sebacate, 2-ethyl hexyl palmitate, isononyl isononanoate, isodecyl isononanoate, isotridecyl isononanoate, 2-ethyl hexyl palmitate, 2-ethyl hexyl stearate, Di-(2-ethyl hexyl)adipate), Di-(2-ethyl hexyl) succinate, isopropyl myristate, isopropyl palmitate, isopropyl stearate, octacosanol, butyl stearate, glyceryl monostearate, polyethylene glycols, oleic acid, triethylene glycol, lanolin, castor oil, acetylated lanolin alcohols, acetylated lanolin, petrolatum, isopropyl ester of lanolin, fatty acids, mineral oils, butyl myristate, isostearic acid, palmitic acid, PEG-23 oleyl ether, olelyl oleate, isopropyl linoleate, cetyl lactate, lauryl lactate, myristyl lactate, quaternised hydroxy alkyl, aminogluconate, vegetable oils, isodecyl oleate, isostearyl neopentanoate, myristyl myristate, oleyl ethoxy myristate, diglycol stearate, ethylene glycol monostearate, myristyl stearate, isopropyl lanolate, paraffin waxes, glycyrrhizic acid, alkyl benzoate, hydrocyethyl stearate amide, and hydrogenated polyisobutene.

In one embodiment, the antiperspirant composition includes glycerin as an emollient.

In other embodiments, the emollient is selected from linear silicones, cyclic silicones, hydrocarbons, polyhydroxy alcohols having more than 3 carbon atoms, liquid or solid polyalkyleneglycol ethers containing a polypropylene glycol (PPG) moiety and terminating in an alkyl ether, and combinations thereof. In another embodiment, the emollient is a nonvolatile silicone, such as dimethiconol or a longer chain dimethicone. For example, the emollient may include dodecamethylpentasiloxane.

In certain embodiment, the emollient may include a cyclomethicone. As used herein "cyclomethicone" refers to the group of methyl siloxanes or cyclic polydimethylsiloxane polymers with low viscosity and high volatility commonly used as skin emollients in personal care formulations. For example, the emollient may include dodecamethylpentasiloxane.

In one embodiment, the antiperspirant composition includes from about 2% to about 20% emollients, based on a total weight of the antiperspirant composition. In other embodiments, the antiperspirant composition may include from about 2 weight % to about 10 weight % emollients. In a preferred embodiment, the antiperspirant composition includes about 5% emollients.

The antiperspirant composition may include a gelling agent typical of antiperspirant compositions. For example, in certain embodiments, the antiperspirant composition may include gelling agents such as, but not limited to, waxes, esters of fatty acid and fatty alcohol, triglycerides, partially or fully hydrogenated soybean oil, partially or fully hydrogenated castor oil, other partial or fully hydrogenated plant oils, stearyl alcohol, or other cosmetically acceptable materials, which are solid or semi solid at room temperature and provide a consistency suitable for application to the skin. The antiperspirant composition may also include a combination of gelling agents. For example, the gelling agent may be a mixture of a high melting point wax(es) and a low melting point wax(es), such as hydrogenated castor oil and stearyl alcohol. In some embodiments, the gelling agent may include cetyl alcohol, and in some embodiments, a glyceryl monostearate mixture may also partially act as a gelling agent.

In one embodiment, the antiperspirant composition includes from about 0.1% to about 5% of a gelling agent, based on a total weight of the antiperspirant composition. In other embodiments, the antiperspirant composition may include from about 1 weight % to about 4 weight % of a gelling agent. In a preferred embodiment, the antiperspirant composition includes about 2.5 gelling agent.

The antiperspirant composition may also include one or more surfactants. In particular, the antiperspirant composition may include one or more surfactants with a high hydrophilic-lipophilic balance (HLB). For example, the antiperspirant composition may include one or more surfactants with an HLB value from about 8 to about 18. In another embodiment, the one or more surfactants may have an HLB value from about 10 to about 18 or from about 15 to 18.

In certain embodiments, the one or more surfactants include at least one of Steareth-21, Steareth-10, Steareth-11, Steareth-13, Steareth-15, Steareth-20, Ceteareth-6, Ceteareth-7, Ceteareth-8, Ceteareth-9, Ceteareth-10, Ceteareth-11, and Ceteareth-12. In some embodiments, the one or more surfactants preferably include Steareth-21.

In other embodiments, the high HLB surfactant may be part of a mixture. For example, in one embodiment, the high HLB surfactant may include polyglyceryl-6 palmitate/succinate. In another embodiment, the one or more surfactants may include a high HLB mixture. For example, the one or more surfactants may include a high HLB glyceryl monostearate mixture. In one embodiment, the high HLB glyceryl monostearate mixture comprises polyglyceryl-6 palmitate/succinate. In another embodiment, the high HLB glyceryl monostearate also includes glyceryl stearate and cetearyl alcohol. In another embodiment, the high HLB glyceryl monostearate has an HLB of about 9. An example of a high HLB glyceryl monostearate mixture usable for some of the embodiments of the present disclosure is available commercially as NATRAGEM EW from Croda Inc., Edison N.J.

In certain embodiments, the one or more surfactants include a high HLB glyceryl monostearate mixture and Steareth-21 at a specific ratio. The antiperspirant composition may include a ratio of the high HLB glyceryl monostearate mixture to Steareth-21 of from 4:1 to 10:1. For example, the ratio of high HLB glyceryl monostearate mixture to Steareth-21 may be 6:1. In one preferred embodiment, the antiperspirant composition may include a 5:1 ratio of a high HLB glyceryl monostearate mixture to Steareth-21.

The antiperspirant composition may include from 1% to 15% surfactant, based on a total weight of the antiperspirant composition. For example, the antiperspirant composition may include from 2 weight % to 10 weight % surfactant. In one preferred embodiment, the antiperspirant composition includes from 4 weight % to about 8 weight % surfactant.

The antiperspirant composition may include one or more antiperspirant actives. In some embodiments, the antiperspirant actives are compatible with the other ingredients in the antiperspirant composition. For example, in some embodiments, the antiperspirant actives are selected to maintain the overall pH of the antiperspirant composition in a range from about 3 to about 5.

In one embodiment, the antiperspirant actives includes at least one of aluminum chlorohydrate (ACH), aluminum chloride, aluminum chlorohydroxide, and aluminum zirconium. For example, the antiperspirant active may be aluminum zirconium tetrachlorohydrex glycine (ZAG).

In some embodiments, the antiperspirant actives are the only active odor control ingredient. For example, in one embodiment, the aluminum zirconium tetrachlorohydrex glycine is the only active odor control ingredient in the antiperspirant composition.

The antiperspirant composition includes an effective amount of antiperspirant actives. For example, the antiperspirant composition may include an amount of antiperspirant actives that is effective to reduce the flow of perspiration in the axillary region. In other embodiments, the antiperspirant composition may include an amount of antiperspirant actives that is effective to reduce malodor or to act as an antibacterial.

The antiperspirant composition may include from about 5% to about 30% antiperspirant actives, based on a total weight of the antiperspirant composition. For example, the antiperspirant composition may include from about 10 weight % to about 25 weight % antiperspirant actives or from about 10 weight % to about 15 weight % antiperspirant actives. In one preferred embodiment, the antiperspirant composition includes about 12 weight % antiperspirant actives. For example, the antiperspirant composition may include from about 10 weight % to about 15 weight % of aluminum zirconium tetrachlorohydrex glycine.

In certain embodiments, the antiperspirant composition may include one or more inert fillers. The inert fillers may be configured to give specific sensorial feelings to the antiperspirant composition when applied. For example, the inert fillers may enhance a dryness sensation or impart a soft, velvety, or powdery feeling to the antiperspirant composition as discerned or perceived by human users.

The inert fillers may include vegetable starches, talc, fumed silica and/or inorganic clays, polyethylene, or mixtures thereof. Preferably, the inert filler, in particulate form, should have physical properties (for example, size, shape, etc.) that are similar to those of the antiperspirant active material (for example, a particulate antiperspirant active metal salt). In one embodiment, the inert filler includes a tapioca starch, which is a starch extracted from cassava root. For example, the inert filler may be a tapioca starch that is hydrophobically modified with polymethylsilsesquioxane.

In certain embodiments, the antiperspirant composition includes additional ingredients. For example, the antiperspirant composition may include fragrances, preservatives, antioxidants, and colorants.

In various embodiments, the antiperspirant composition may include one or more preservatives. In some embodiments, the preservatives improve an antimicrobial characteristic of the antiperspirant composition to improve storage life or prevent decay of the composition. In other embodiments, the preservatives may also enhance the functional characteristics of the antiperspirant composition. For example, in some embodiments, the preservative may provide deodorant or emollient effects to the antiperspirant composition.

In various examples of embodiments, the one or more preservatives include at least one of phenoxyethanol, caprylyl glycol, ethylhexylglycerin, citric acid, benzoic acid, lactic acid, and combinations thereof. In other embodiments, the one or more preservatives consist essentially of only one of phenoxyethanol, caprylyl glycol, ethylhexylglycerin, citric acid, benzoic acid, or lactic acid, with only trace amounts of other preservative materials. In one example of such an embodiment, the composition contains one preservative, where the preservative consists of at least 99% of only one of phenoxyethanol, caprylyl glycol, ethylhexylglycerin, citric acid, benzoic acid, or lactic acid.

In certain embodiments, the preservative may include one or more antioxidant. For example, antioxidants may be added to the antiperspirant composition to act as ingredient protectants and for maintenance of long-term stability of the composition. Suitable antioxidants include Tinogard, manufactured by Ciba Specialty Chemicals, Basel, Switzerland.

The antiperspirant composition may include an effective amount of preservatives. For example, the antiperspirant composition may include an amount of preservatives effective to reduce a spoilage of the antiperspirant composition during storage or use.

In some embodiments, the antiperspirant composition may optionally include one or more fragrances. A variety of fragrances can be used in the antiperspirant compositions if a scented product is desired. For example, in some embodiments, any fragrance suitable for personal care use may be incorporated into the antiperspirant composition as a non-essential ingredient.

EXAMPLES

Aspects of the present disclosure may be further understood by referring to the following examples. The examples are illustrative, and are not intended to be limiting embodiments thereof. Table 1 illustrates an antiperspirant composition according to an embodiment of the present disclosure.

TABLE 1

| Composition 1 | |
| --- | --- |
| Aluminum zirconium tetrahydrex glycine | 37.5% (12% ZAG active) |
| Water | 33.2% |
| Glycerin | 10% |
| Glyceryl monostearate mixture | 6% |
| Steareth-21 | 1% |
| Cetyl alcohol | 2.5% |
| Isopropyl myristate | 2.5% |
| dodecamethylpentasiloxane | 2% |
| Caprylyl glycol | 0.3% |
| Tapioca starch | 5% |
| Total | 98.9% |

The composition of Table 1 was then evaluated by a sensory expert panel against three commercially available antiperspirant compositions that contain the same or higher weight percentages of antiperspirant active: Comparative Composition A (12% ACH), Comparative Composition B (12% ACH), and Comparative Composition C (20% ZAG). The expert panel evaluated the four compositions to compare and judge the amount and whiteness of any residue left immediately after application to skin and three minutes after application to skin. The expert panel similarly evaluated the compositions with regard to the amount and whiteness of any white residue visible on a black cloth immediately after application to the cloth.

In particular, the expert panel evaluated the compositions on a 0-15 attribute scale in an underarm evaluation procedure. Ten judges evaluated the sensory properties for each of the composition of Table 2, with each panelist assessing each product two times following a standard sensory testing procedure using the 0-15 attribute scale. The samples were blinded and coded with a random three-digit number. The order of sample presentation was similarly balanced and randomized across all the panelists.

To test the compositions, the judges were asked to pre-wash their underarm areas and apply specified amounts of each of the compositions of Table 2. The judges then evaluated the compositions of Table 2 on skin whiteness as a measurement of clarity and residue left behind immediately after application and after 3 minutes. Rub-off white Residue and other residue was also evaluated as applied on a black cloth.

TABLE 2

| | Composition 1 (12% ZAG) | Comparative Composition A (12% ACH) | Comparative Composition B (12% ACH) | Comparative Composition C (20% ZAG) |
|---|---|---|---|---|
| Skin Whiteness (immediate) | 0.6 | 2.7 | 2.9 | 1.1 |
| Skin Whiteness (after 3 mins.) | 0.0 | 1.2 | 1.1 | 0.1 |
| Black cloth Whiteness (immediate) | 0.6 | 2.9 | 3.3 | 1.3 |

As illustrated in Table 1, exemplary composition 1 had significantly lower values for white residue visibility both when applied to skin and when applied to a black cloth as compared to the commercial Comparative Compositions A-C. Accordingly, even though composition 1 is an opaque cream before application, it produces an amount of white residue that is at least 45% less visible than the other compositions after application. Without being bound by theory, the reduced amount of residue provided by exemplary composition 1 may be attributable to differences in the refractive index of ZAG and ACH.

The stability of antiperspirant compositions according to the present disclosure, such as that of Table 1, was measured before aging and after aging at 40° C. for up to 13 weeks, which is the extent of time commonly used to predict a 24 month shelf life under normal conditions. The composition of Table 1 displayed no spoilage or significant degradation in antiperspirant efficiency after aging. In addition, the composition of Table 1 displayed no separation after repeated freeze/thaw cycles during extended storage.

The present disclosure has been described with reference to exemplary embodiments. Although a limited number of embodiments have been shown and described, it will be appreciated by those skilled in the art that changes may be made in these embodiments without departing from the principles and spirit of preceding detailed description. It is intended that the present disclosure be construed as including all such modifications and alterations insofar as they come within the scope of the appended claims or the equivalents thereof.

What is claimed is:

1. An opaque antiperspirant composition, comprising:
    an antiperspirant active comprising from 10 weight % to 15 weight % of aluminum zirconium tetrachlorohydrex glycine, based on a total weight of the opaque antiperspirant composition;
    a high HLB surfactant with an HLB value from 8 to 18;
    an emollient that comprises 10 weight % glycerin, 2.5 weight % cetyl alcohol, 2.5 weight % isopropyl myristate, and 2 weight % dodecamethylpentasiloxane based on the total weight of the antiperspirant composition;
    from 30 weight % to 35 weight % of water, based on the total weight of the antiperspirant and/or deodorant composition;
    a preservative selected from phenoxyethanol, caprylyl glycol, ethylhexylglycerin, citric acid, benzoic acid, lactic acid, and combinations thereof; and
    an inert filler selected from vegetable starches, talc, fumed silica and/or inorganic clays, polyethylene, or mixtures thereof;
    wherein the high HLB surfactant comprises a high HLB glyceryl monostearate mixture and at least one of Steareth-21, Steareth-10, Steareth-11, Steareth-13, Steareth-15, Steareth-20, Ceteareth-6, Ceteareth-7, Ceteareth-8, Ceteareth-9, Ceteareth-10, Ceteareth-11, and Ceteareth-12,
    wherein the high HLB glyceryl monostearate mixture comprises polyglyceryl-6 palmitate/succinate, and
    wherein the composition comprises from 4 weight % to 8 weight % of the high HLB surfactant, based on the total weight of the antiperspirant composition.

2. The opaque antiperspirant composition of claim 1, wherein the high HLB surfactant further comprises Steareth-21, and wherein a weight ratio of the high HLB glyceryl monostearate mixture to the Steareth-21 is from 4:1 to 10:1.

3. The opaque antiperspirant composition of claim 1, wherein the inert filler comprises a vegetable starch.

4. The opaque antiperspirant composition of claim 1, wherein the inert filler comprises at least one of tapioca starch and silica.

5. The opaque antiperspirant composition of claim 1, wherein the opaque antiperspirant composition comprises from 2 weight % to 20 weight % of the emollient, based on the total weight of the opaque antiperspirant composition.

6. The opaque antiperspirant composition of claim 1, wherein the high HLB surfactant consists essentially of a mixture of Steareth-21 and a high HLB glyceryl monostearate mixture.

7. The opaque antiperspirant composition of claim 1, comprising:
    from 2 weight % to 20 weight % of the emollient, based on the total weight of the antiperspirant composition; and
    an inert filler.

8. The antiperspirant composition of claim 7, wherein the high HLB surfactant consists essentially of a mixture of Steareth-21 and a high HLB glyceryl monostearate mixture.

9. The opaque antiperspirant composition of claim 1, comprising 37.5% aluminum zirconium tetrahydrex glycine (12% ZAG active) as the antiperspirant active, based on the total weight of the antiperspirant composition.

10. The opaque antiperspirant composition of claim 1, comprising 0.3% caprylyl glycol as the preservative, based on the total weight of the antiperspirant composition.

11. The opaque antiperspirant composition of claim 10, further comprising 5% tapioca starch as the inert filler, based on the total weight of the antiperspirant composition.

12. The opaque antiperspirant composition of claim 1, comprising 37.5% aluminum zirconium tetrahydrex glycine (12% ZAG active) as the antiperspirant active; 33.2% water as the carrier; a mixture of 10% glycerin, 2.5% cetyl alcohol, 2.5% isopropyl myristate, and 2% dodecamethylpentasiloxane as the emollient; a mixture of 6% glyceryl monostearate mixture and 1% Steareth-21 as the high HLB surfactant; 0.3% caprylyl glycol as the preservative; and 5% tapioca starch as the inert filler; based on the total weight of the antiperspirant composition.

\* \* \* \* \*